United States Patent [19]

Maurer

[11] Patent Number: 4,873,996
[45] Date of Patent: Oct. 17, 1989

[54] VAGINAL STIMULATOR FOR CONTROLLING URINARY INCONTINENCE IN WOMEN

[75] Inventor: Donald D. Maurer, Anoka, Minn.

[73] Assignee: Empi, Inc., St. Paul, Minn.

[21] Appl. No.: 233,232

[22] Filed: Aug. 18, 1988

Related U.S. Application Data

[62] Division of Ser. No. 916,118, Oct. 6, 1986, Pat. No. 4,785,828.

[51] Int. Cl.$^4$ .............................................. A61F 13/00
[52] U.S. Cl. ..................................... 128/844; 128/788
[58] Field of Search ................... 128/79, 830, 842–844, 128/883, 884, 303.17, 788; 640/349

[56] References Cited

U.S. PATENT DOCUMENTS

| | | | |
|---|---|---|---|
| 3,080,865 | 3/1963 | Vincent | 128/98 |
| 3,417,743 | 12/1968 | Carrera | 128/79 |
| 3,528,423 | 9/1970 | Lee | 128/295 |
| 3,554,184 | 1/1971 | Habib | 128/1 |
| 3,646,616 | 3/1972 | Keshin | 128/283 |
| 3,661,155 | 5/1972 | Lindan | 128/295 |
| 3,705,575 | 11/1972 | Edwards | 118/1 R |
| 3,744,063 | 7/1973 | McWhorter et al. | 128/1 R |
| 3,800,800 | 4/1974 | Garbe et al. | 128/408 |
| 3,866,613 | 2/1975 | Kenny et al. | 128/408 |
| 3,870,051 | 3/1975 | Brindley | 128/422 |
| 3,926,178 | 12/1975 | Feldzamen | 128/2 S |
| 3,933,147 | 1/1976 | DuVall et al. | 128/2 S |
| 3,973,571 | 8/1976 | Subel | 128/408 |
| 4,019,498 | 4/1977 | Hawtrey et al. | 128/1 R |
| 4,139,006 | 2/1979 | Corey | 128/127 |
| 4,153,059 | 5/1979 | Fravel et al. | 128/422 |
| 4,290,420 | 9/1981 | Manetta | 128/1 R |
| 4,296,760 | 10/1981 | Carlsson et al. | 128/788 |
| 4,349,031 | 9/1982 | Perlin | 128/642 |
| 4,387,719 | 6/1983 | Plevnik et al. | 128/421 |
| 4,431,001 | 2/1984 | Hakansson et al. | 128/421 |
| 4,457,299 | 7/1984 | Cornwell | 128/1 R |
| 4,515,167 | 5/1985 | Hochman | 128/736 |
| 4,532,924 | 8/1985 | Auth et al. | 128/303.17 |
| 4,568,339 | 2/1986 | Steer | 604/329 |
| 4,580,578 | 4/1986 | Barsom | 128/784 |

FOREIGN PATENT DOCUMENTS

| | | |
|---|---|---|
| 101595 | 2/1984 | European Pat. Off. |
| 2547203 | 12/1984 | France |

Primary Examiner—Max Hindenburg
Attorney, Agent, or Firm—Kinney & Lange

[57] ABSTRACT

A vaginal stimulator adapted to be inserted into a woman's vagina to stimulate and constrict muscles therein and prevent the flow of urine through the urethra. A vaginal plug having a conical tip includes a power supply, pulse generator, on/off switch and intensity control switch mounted therein. Electrodes coupled to the pulse generator are positioned on an exterior surface of the vaginal plug. A disposable condom is unrolled over the vaginal plug and includes conductive elements which are positioned in electrical contact with the electrodes to carry the electric pulses to the muscles.

4 Claims, 2 Drawing Sheets

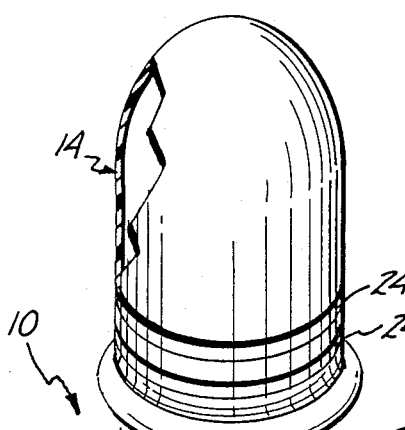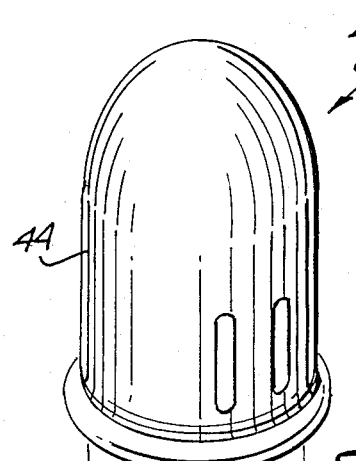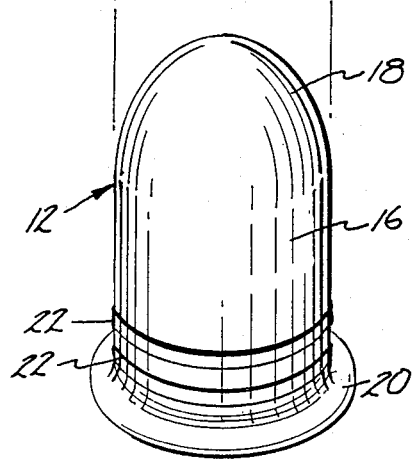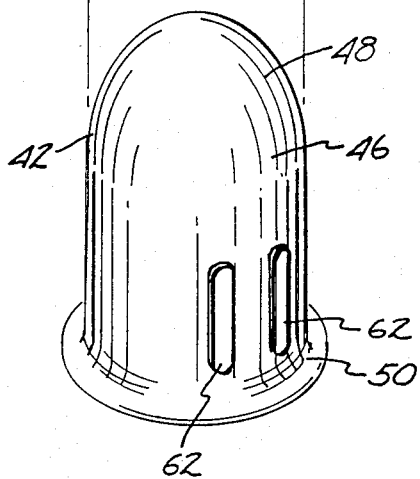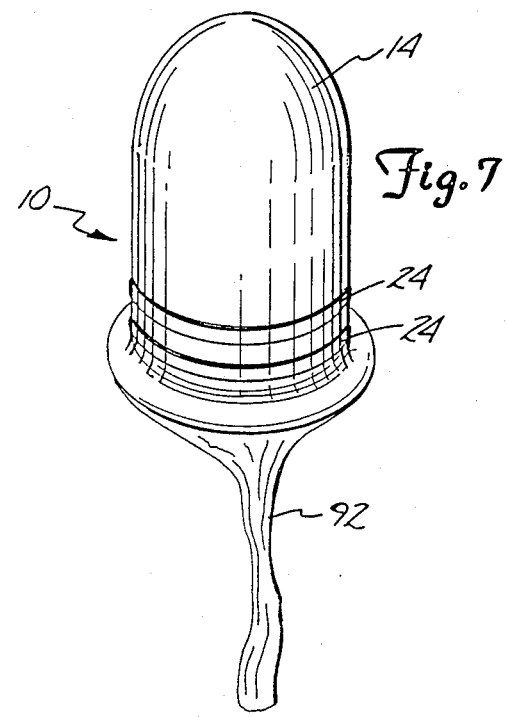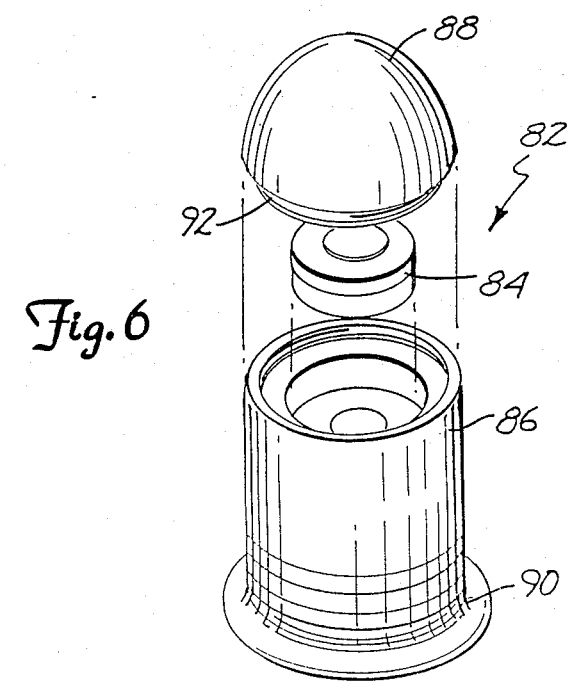

VAGINAL STIMULATOR FOR CONTROLLING URINARY INCONTINENCE IN WOMEN

This is a division of application Ser. No. 916,118 filed Oct. 6, 1986, now U.S. Pat. No. 4,785,828.

BACKGROUND OF THE INVENTION

1. Field of the Invention.

The present invention relates to electrical neuromuscular stimulators. In particular, the present invention is a two-piece self-contained stimulator for controlling urinary incontinence in women.

2. Description of the Prior Art.

Neuromuscular electrical stimulation, whereby motor nerve fibers are electrically stimulated by means of transcutaneously applied pulses of electrical current to cause contraction of muscles the fibers innervate, is widely used to assist persons afflicted with motor dysfunctions in performing muscle contraction maneuvers. This technique is also used to re-educate patients in the proper use of the dysfunctional muscles.

In cases in which urinary incontinence in women is caused by the patient's inability to properly contract the external sphincter of the urethra, it has been shown that a neuromuscular stimulator can effectively prevent the unwanted flow of urine. Furthermore, use of such a stimulator can re-educate the patient to voluntarily or automatically impede the flow of urine. After a period of time in which the stimulator is used, a woman will be able to maintain herself dry without continued use of the device.

Existing stimulators used to control urinary incontinence are not well accepted because they are difficult and/or messy to use, and constitute an unrewarding method for controlling urinary incontinence. Known devices consist of a vaginal plug with one or more electrodes in the form of metallic rings. When the plug is inserted, the electrodes contact the vagina wall. A cable extends from the plug to a stimulator which is typically worn externally, such as being attached to clothing. The presence of the wire is inconvenient, as is the insertion, extraction and cleaning of the plug.

Clearly, there is a continuing need for improved vaginal stimulators which can be used to prevent the unwanted flow of urine. In addition to being effective, the stimulator must be convenient to use. The device must therefore be easy to insert and extract. To ensure proper hygiene, the stimulator should also be capable of being easily cleaned.

SUMMARY OF THE INVENTION

The present invention is a vaginal stimulator adapted to be inserted into a woman's vagina to stimulate and constrict muscles therein and prevent the flow of urine through the urethra. One embodiment includes a vaginal plug which includes terminals for receiving a train of electric pulses, and electrodes on an exterior surface of the plug which are coupled to the terminals. A condom adapted to surround the vaginal plug includes conductive elements positioned in electrical contact with the electrodes to carry the electric pulses to the muscles.

In preferred embodiments, a power supply, pulse generator means, on/off switch, and intensity control switch are mounted within the vaginal plug. The vaginal plug can be fabricated of insulating polymer material. The condom can be fabricated of latex, with conductive polymer elements molded therein.

The vaginal stimulator of the present invention is convenient and easy to use. Before each use, the condom is simply rolled over the plug, and the conductive elements positioned adjacent the electrodes. Once inserted into the vagina, the stimulator can be turned on and off as required. The device also affords a high degree of hygiene since the condom keeps the plug clean and dry, and can be of disposed of after use.

BRIEF DESCRIPTION OF THE DRAWINGS

FIG. 1 is an exploded view illustrating the plug and condom of a first vaginal stimulator in accordance with the present invention.

FIG. 4 is an exploded view illustrating the vaginal plug and condom of a second vaginal stimulator in accordance with the present invention.

FIG. 6 is an exploded view of a vaginal plug in accordance with yet another embodiment of the present invention.

FIG. 7 is a view illustrating the vaginal plug shown in FIG. 1 in its assembled form.

DETAILED DESCRIPTION OF THE PREFERRED EMBODIMENTS

Figure 2:
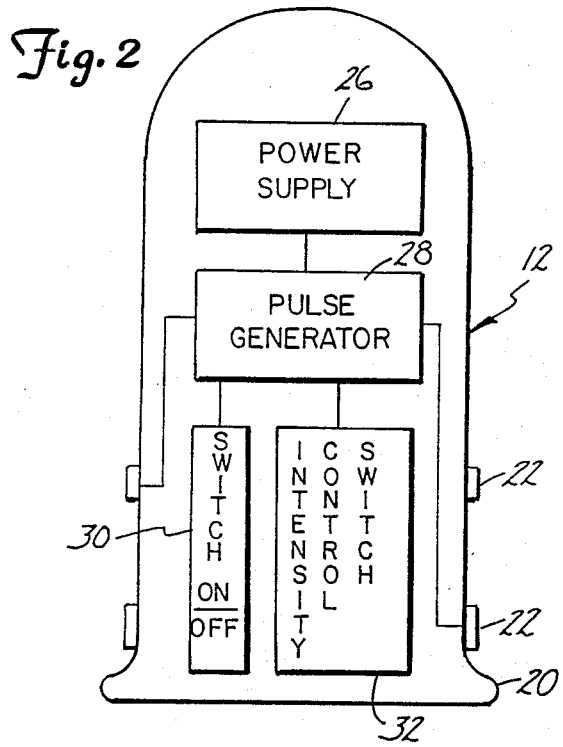
FIG. 2 is a schematic diagram illustrating stimulator circuitry within the vaginal plug shown in FIG. 1.

The present invention is a two-piece self-contained vaginal stimulator for controlling urinary incontinence in women. When inserted into the vagina and actuated, the stimulator produces a train of electric pulses which cause a contraction of muscles of the pelvic floor. The external sphincter of the urethra is thereby constricted, preventing the unwanted flow of urine. The device is simple and hygienic to use.

A first embodiment of the present invention, vaginal stimulator 10, is illustrated in FIG. 1. As shown, stimulator 10 includes vaginal plug 12 and condom 14. Plug 12 is adapted to fit within a woman's vagina and includes a cylindrical body 16 with a cone-shaped tip 18 and ridged distal end 20. A pair of annular or ring-shaped electrodes 22 are positioned on an exterior surface of plug 12 and surround body portion 16 near distal end 20. Electrodes 22 are also parallel to one another in the embodiment shown, and extend from the exterior surface of plug 12. In one embodiment electrodes 22 are fabricated of metal. Plug 12 can be fabricated of an insulating polymer such as epoxy coated with silicone rubber.

Condom 14 is adapted to ensheath plug 12 and can be fabricated of latex or similar soft pliable and impermeable material. A pair of conductive sections or elements 24 are fabricated within the otherwise insulating material of condom 14, and are positioned in such a manner that they will be aligned with and fit adjacent to electrodes 22 when the condom is inserted onto plug 12. Conductive sections 24 are annular in the embodiment shown and spaced from one another so as to contact ring-shaped electrodes 22. Conductive sections 24 can, for example, be fabricated of conductive rubber, plastic or other polymer material which is molded into condom 14 during manufacture. For convenience, condom 14 can be rolled up prior to use, and is shown partially rolled up in FIG. 1.

Stimulator circuitry including power supply 26, pulse generator and associated control circuitry 28, on/off switch 30, and intensity control switch 32 are shown sealed within plug 12 in FIG. 2. Power supply 26 can include batteries or any other desired source of power. When on/off switch 30 is actuated by a woman wearing stimulator 10, pulse generator 28 will produce a series of pulse trains at its output terminals. The pulse trains are coupled from the output terminals to the electrodes by leads as shown. In one embodiment pulse generator 28 produces five second 30 Hz pulse train bursts followed by twenty second rest periods. Each pulse train burst includes a one second oneset region during which intensity of the pulses increases to a selected maximum intensity, and a one second termination region at the end during which the intensity of the pulses decreases to zero.

Figure 3:
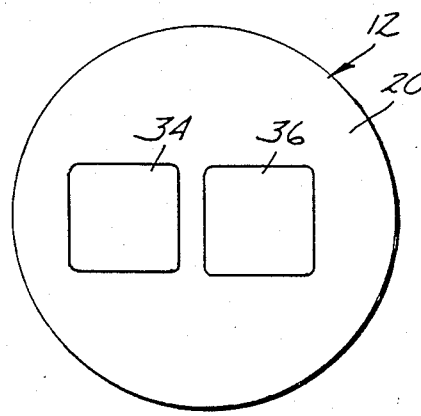
FIG. 3 is an end view of the vaginal plug shown in FIG. 1.

Intensity control switch 32 is actuated to select the maximum pulse intensity for optimum performance. Intensity control switch 32 and pulse generator 28 can be designed in such a manner that sequential actuation of the switch will increase the maximum intensity in discrete steps until switching from a highest intensity to a lowest intensity. Switches 30 and 32 can be membrane-type switches located near distal end 20 of plug 12. As shown in FIG. 3, switches 30 and 32 can then be actuated through soft spots 34 and 36, respectivaely, in the material forming plug 12 while the stimulator is being worn.

A second embodiment of the present invention, vaginal stimulator 40, is illustrated in FIG. 4. Stimulator 40 includes a vaginal plug 42 and condom 44. Plug 42 can be shaped identical to plug 12 previously described, and includes a cylindrical body portion 46, a conical tip 48 and a ridged distal end 50. A pair of electrodes 62 are positioned on an exterior surface and extend in a longitudinal direction along body portion 46. Condom 44 can be identical to that of condom 14 of stimulator 10 described previously, with the exception that its conductive elements 64 are positioned along a longitudinal axis of the condom so as to come into alignment and electric contact with electrodes 62 when the condom is positioned on plug 42.

Figure 5:
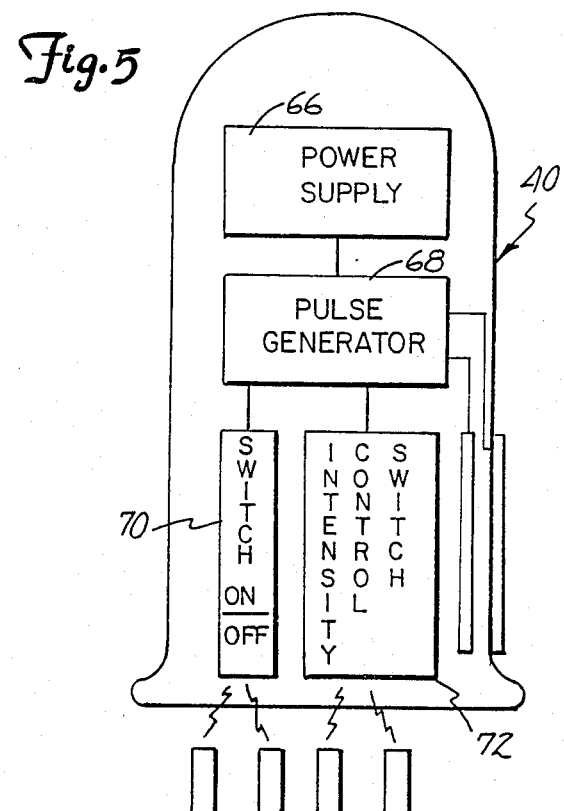
FIG. 5 is a block diagram representation of stimulator circuitry within the vaginal plug shown in FIG. 4.

Stimulator circuitry for stimulator 40 is illustrated in FIG. 5. As shown, stimulator 40 includes a power supply 66, pulse generator and associated control circuitry 68, on/off switch 70, and intensity control switch 72. Power supply 66 and pulse generator 68 can be identical to those previously described with reference to stimulator 10. Switches 70 and 72 are magnetic proximity switches in the embodiment shown, and are actuated by magnets 71 and 73, respectively. Aside from the fact that they are actuated by magnets, switches 70 and 72 function in a manner identical to that of switches 30 and 32, respectively, previously described with reference to stimulator 10.

The stimulation circuitry of vaginal stimulators 10 and 40 is preferably sealed within their respective plugs 12 and 42 during manufacture. Batteries or other power supply 26 will be capable of powering these devices for an extended period of time, after which they can be discarded. Vaginal plug 82, an alternative reuseable version of plugs 12 and 42 and illustrated in FIG. 6, utilizes a rechargeable or replaceable battery 84. To permit replacement of battery 84, plug 82 includes a cylindrical body 86, removable conical tip 88, and ridged distal end 90. Tip 88 has a threaded shaft 92 which can be screwed into threaded opening 94 of body 86. Tip 88 can thereby be removed when battery 84 is drained, permitting the battery to be recharged and/or replaced. Stimulator circuitry (not shown), as well as construction of plug 82, can be identical to that of plugs 12 and 42 previously described.

The assembly of vaginal stimulator 10, which is also representative of the assembly of vaginal stimulator 40, is illustrated in FIG. 7. Condom 14 will be positioned over the tip (not visible in FIG. 7) of plug 12, and is unrolled so as to completely enclose or ensheath the plug. A trailing end 92 of condom 14 will extend beyond the distal end of plug 12. Care must be taken to properly align conductive elements 24 of condom 14 with the electrodes (not visible) of plug 12.

Figure 8:
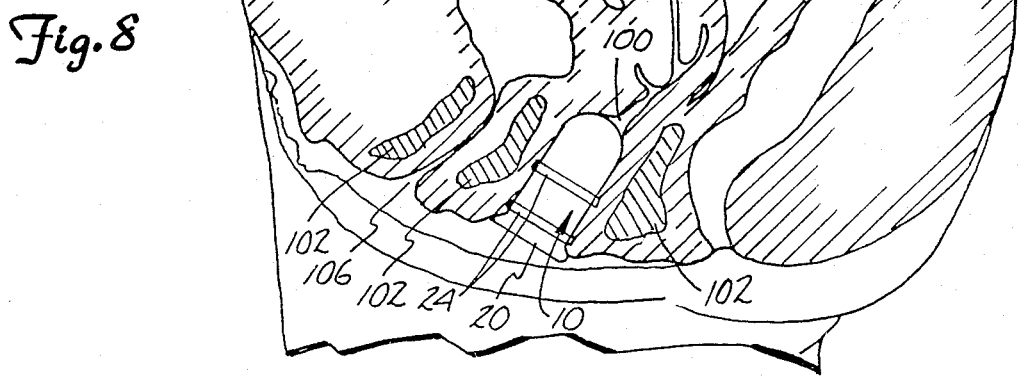
FIG. 8 is a sectional view illustrating the placement of the stimulator within a woman's vagina.

Once assembled, stimulator 10 can be inserted into a woman's vagina 100 with ridged distal end 20 fitting even with the introitus as shown in FIG. 8. Conductive sections 24 of stimulator 10 will then be in physical contact with tissue surrounding various muscles 102, including the external sphincter muscle, within the woman's pelvic region. On/off switch 30 can be actuated by pressing region 34 on distal end 20 (FIG. 3) with a finger. In a similar manner, region 36 can be pressed to adjust intensity of the pulses generated. These pulses will then stimulate muscles 102 surrounding urethra 104 in such a manner that they will constrict and close off the urethra to prevent the flow of urine from bladder 106. Before urinating, stimulator 10 can be turned off by actuating switch 30.

The stimulators of the present invention present a simple and hygienic method of controlling urinary incontinence. Prior to each use a new condom is placed over the plug, and the assembled stimulator positioned in the vagina. The stimulator can then be actuated and deactuated while in place. The trailing end of the condom can be used as a handle to facilitate removal of the stimulator. The condom can then be removed and disposed of. Since the plug does not come into contact with the vagina, it remains dry and clean.

Although the present invention has been described with reference to preferred embodiments, workers skilled in the art will recognize that changes may be made in form and detail without departing from the spirit and scope of the invention.

What is claimed is:

1. A condom which can be removably unrolled onto a vaginal plug of the type having electrodes on an exterior surface of the plug, wherein the condom is collapsible, fabricated of stretchable, pliable and impermeable material, and includes at least one pair of spaced-apart conductive elements positioned so as to be in electrical contact with the electrodes when the condom is unrolled onto the plug.

2. The condom of claim 1 wherein the conductive elements include a pair of annular conductive elements.

3. The condom of claim 1 wherein the conductive elements include a pair of linear conductive elements oriented parallel to a longitudinal axis of the condom.

4. The condom of claim 1 wherein the conductive elements are conductive polymer elements.

* * * * *